US009951000B2

(12) United States Patent
Peng et al.

(10) Patent No.: US 9,951,000 B2
(45) Date of Patent: Apr. 24, 2018

(54) FLORFENICOL SYNTHESIZING METHOD

(71) Applicant: MASTEAM BIO-TECH CO. LTD., Wuxue (CN)

(72) Inventors: Yaowu Peng, Wuxue (CN); Wenjing Tian, Wuxue (CN); Qing Ye, Wuhan (CN); Zhicheng Fang, Wuhan (CN)

( * ) Notice: Subject to any disclaimer, the term of this patent is extended or adjusted under 35 U.S.C. 154(b) by 0 days.

(21) Appl. No.: 15/206,553

(22) Filed: Jul. 11, 2016

(65) Prior Publication Data
US 2016/0318859 A1    Nov. 3, 2016

Related U.S. Application Data

(63) Continuation-in-part of application No. PCT/CN2014/075432, filed on Apr. 16, 2014.

(51) Int. Cl.
*C07C 315/04* (2006.01)
*C07D 263/10* (2006.01)
*C07D 263/20* (2006.01)

(52) U.S. Cl.
CPC .......... *C07C 315/04* (2013.01); *C07D 263/10* (2013.01); *C07D 263/20* (2013.01)

(58) Field of Classification Search
None
See application file for complete search history.

(56) References Cited

U.S. PATENT DOCUMENTS 5,352,832 A * 10/1994 Wu ................. C07C 315/04
                                              548/215
5,789,599 A *  8/1998 Davis ............... C07C 315/02
                                              548/955

FOREIGN PATENT DOCUMENTS

CN    102827042    * 12/2012

OTHER PUBLICATIONS

Lu ("Synthesis of Florfenicol" Chinese Journal of Pharmaceuticals, 2010, 41 (7), p. 481-484,).*
Yun ("Efficient Synthe" is of Enantiomerically Pure 2-Acylaziridines: Facile Synthesis of N-Boc-safingol, N-Boc-d-erythro-spinganine, and N-Boc-spisulosine from a common intermediate J. Org. Chem. 2003, 68, 7675-7680).*

\* cited by examiner

*Primary Examiner* — Jafar Parsa
*Assistant Examiner* — Amy C Bonaparte
(74) *Attorney, Agent, or Firm* — Wayne & Ken, LLC; Tony Hom

(57) ABSTRACT

A method for synthesizing florfenicol comprises the steps of cyclization, selective reduction, fluorination, ring opening, deprotection, acylation, esterification with sulfonic acids, epimerization and hydrolysis. Florfenicol is prepared by successively purifying, selectively reducing, and epimerizing chiral (R)-amino ketones. This improves atom economy, reduces waste water pollution and accordingly reduces costs for treating waste water and pollution to the environment, thus lowering costs and simplifying the process. Furthermore, triethylamine hydrofluoride is used as a fluorinating reagent, resulting in improved safety, because of the use of liquid reaction conditions as compared to gaseous reaction conditions, and reduced corrosion to the reaction equipment.

13 Claims, No Drawings

FLORFENICOL SYNTHESIZING METHOD

CROSS-REFERENCE TO RELATED APPLICATIONS

This application is a continuation in part of International Patent Application No. PCT/CN2014/075432 with a filing date of Apr. 16, 2014, designating the United States, now pending. The content of the aforementioned application, including any intervening amendments thereto, is incorporated herein by reference.

TECHNICAL FIELD

The present invention relates to a synthesizing method of veterinary drug florfenicol, which belongs to the technical field of the synthesis of active pharmaceutical ingredients.

BACKGROUND OF THE PRESENT INVENTION

Florfenicol is a dedicated animal chloramphenicol broad-spectrum antibiotic researched and developed by Nagabhushan of Schering-Plough Company in USA at the end of 1970s. In view of the prevention and treatment of animal diseases, the efficacy of florfenicol is better than that of chloramphenicol and thiamphenicol, so that the florfenicol has wider application prospect, and the synthesis of the florfenicol is always greatly emphasized.

At present, there are mainly two methods for industrially producing the florfenicol both at home and abroad: 1, D-4-Methylsulfonylphenyl serine ethyl ester is sequentially subjected to a reduction reaction, a reaction with benzonitrile to prepare oxazoline, a fluorination reaction in the existence of an Ishikawa reagent, a hydrolysis reaction, and a dichloro acylation reaction to obtain the florfenicol, namely, a synthetic route 1; 2, D-4-Methylsulfonylphenyl serine ethyl ester is sequentially subjected to the reduction reaction, the reaction with dichloroacetonitrile to generate oxazoline, the fluorination reaction in the existence of the Ishikawa reagent and the hydrolysis reaction to obtain the florfenicol, namely, a synthetic route 2. The dichloro acylation reaction is omitted in route 2 relative to route 1, so that route 2 effectively reduces production and operation steps and cost.

Synthetic Route 1:

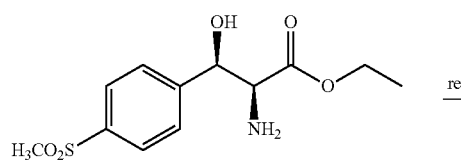

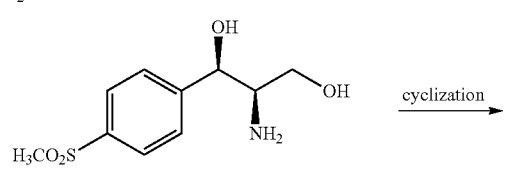

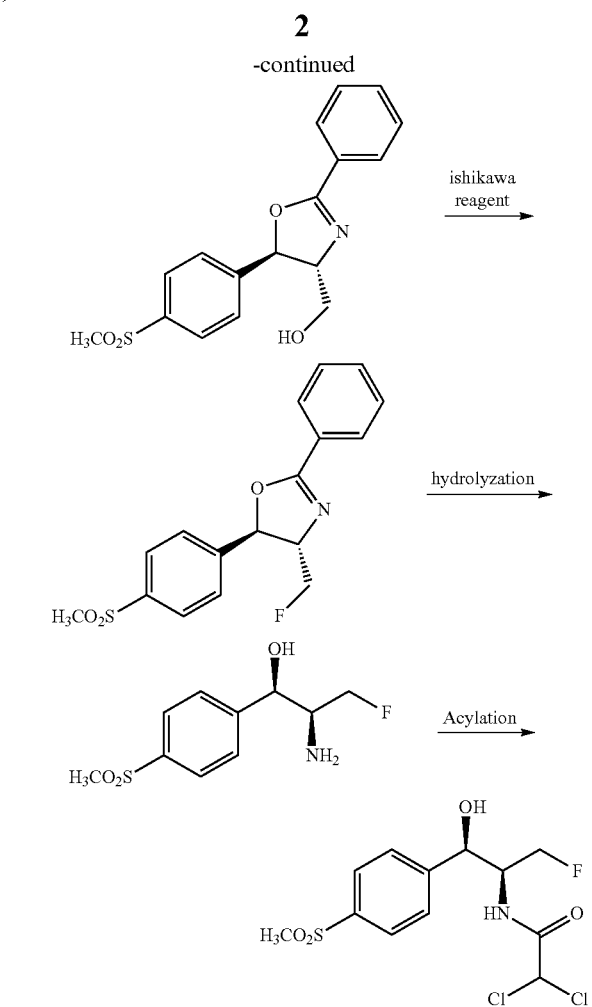

Route diagram 2:

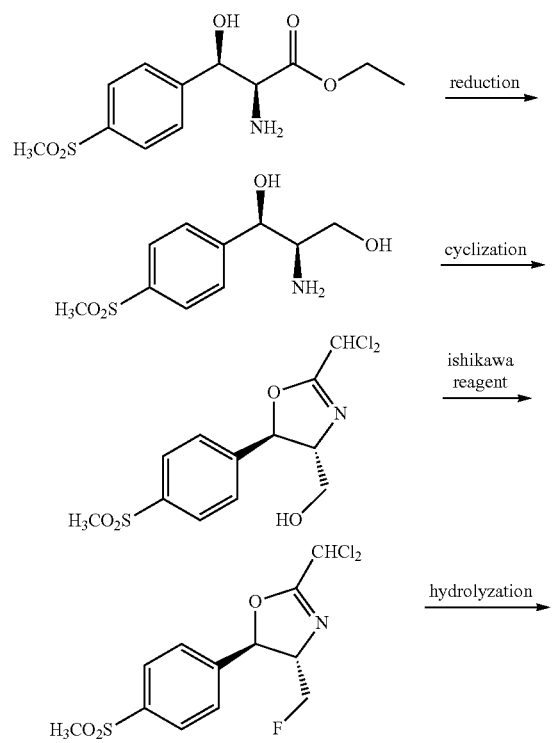

-continued

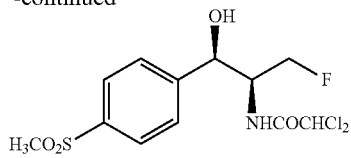

D-4-Methylsulfonylphenyl serine ethyl ester is used in the above-mentioned two synthetic routes; however, the existing industrial method for preparing the compound is still to adopt tosyl chloride as a starting raw material to have the reduction reaction, a methylation reaction, a bromination oxidation reaction and the hydrolysis reaction to obtain P-methylsufonyl benzaldehyde, then the P-methylsufonyl benzaldehyde is used for reacting with glycine and copper sulfate to prepare a copper salt, and the copper salt has an esterification reaction and is resolved by tartaric acid to obtain D-4-Methylsulfonylphenyl serine ethyl ester, namely, a synthetic route 3.

preparing the florfenicol through the asymmetric reduction reaction by utilizing the chiral catalyst: CN102827042A discloses a scheme for taking thioanisole as a starting raw material to synthesize the compound [1-benzylaziridin-2-yl] [4-(methylmercapto)phenyl]ketone through the three-step chemical reaction, further for performing the asymmetric hydrogenation reduction reaction for a product by utilizing the chiral catalyst to obtain [1-benzylaziridin-2-yl][4-(methylmercapto)phenyl]methanol, and further for preparing the florfenicol by means of several chemical reactions, wherein the chiral catalyst used in the scheme is trans-RuCl2[(R)-xylbinap][(S)-DPEN]. In the scheme, chiral central carbon is built by utilizing the asymmetric reduction reaction of the chiral catalyst, so that the chiral resolution is avoided. However, the chiral catalyst itself has the weaknesses of difficulty in preparation and storage, easiness in inactivation in industrial production, etc., further resulting in high application cost and disadvantage to the industrialized produc- Synthetic Route 3:

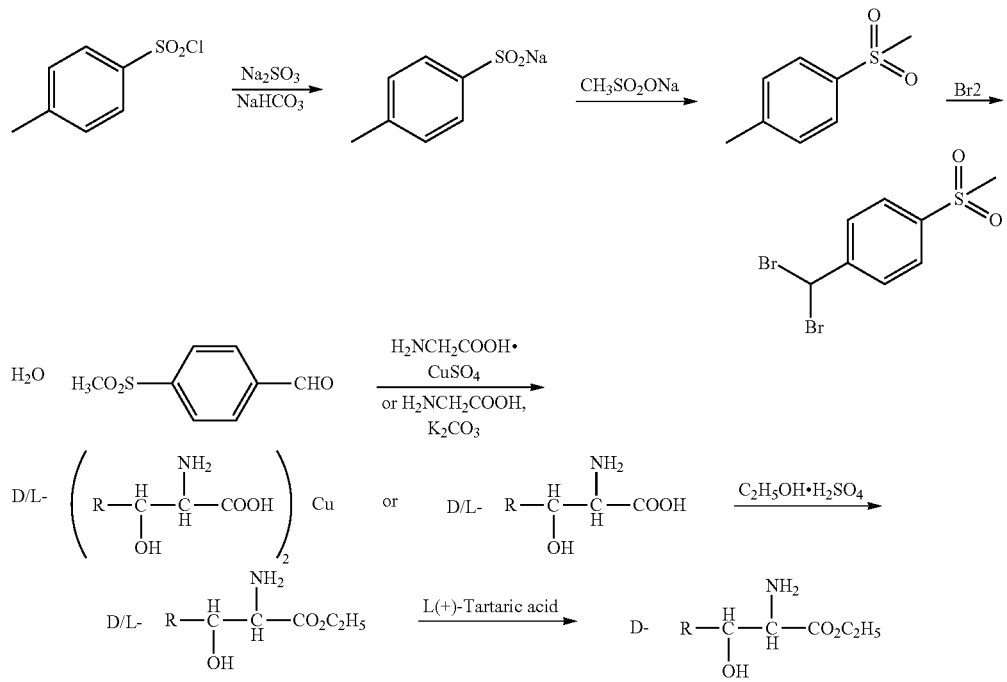

The production technique involved in route 3 can produce a great amount of copper sulfate waste water in the production process, so that the treatment cost of the waste water is very high; moreover, 50% raw materials are wasted due to the chiral resolution on the aspect of the atomic economy, and production and operation are time-consuming; and the introduction of fluorine atoms uses the Ishikawa reagent which can severely corrode the equipment and is relatively high in cost.

In recent years, the research on the asymmetric reduction synthesis of a chiral compound by utilizing a chiral catalyst is widely performed, and relevant research on the florfenicol is also carried out. The applicant devotes to the research on tion. In view of this, it is very necessary to find a production route more suitable for industrialization.

SUMMARY OF THE PRESENT INVENTION

The present invention aims at providing a new florfenicol synthesizing method. The synthesizing method of the florfenicol comprises the following steps:

(1) dissolving 2-bromo-3-chloro-1-[4-(methylmercapto) phenyl]-1-acetone in an organic solvent, adding an oxidation catalyst and adding hydrogen peroxide for facilitating the reaction to prepare 2-bromo-3-chloro-1-[4-(methylsulfonyl) phenyl]-1-acetone;

(2) dissolving the 2-bromo-3-chloro-1-[4-(methylsulfonyl)phenyl]-1-acetone, $R_1$—$NH_2$ (chiral amine) and base in the solvent, reacting at 0 to 30 DEG C. to prepare a chiral aminoketone compound of a diastereoisomer, and performing a physical separation method on the chiral aminoketone compound of the diastereoisomer to obtain an R-configuration aminoketone compound 1: 1-$R_1$-2-(R)-[4-(methylsulfonyl)phenyl]formyl aziridine;

compound 1

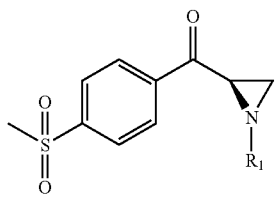

wherein $R_1$ is (S)-1-phenethyl or (R)-1-phenethyl;

(3) dissolving the 1-$R_1$-2-(R)-[4-(methylsulfonyl)phenyl] formyl aziridine in an organic solvent, cooling, and then reacting with a hydride reagent and lewis acid to obtain a single-configuration chiral amino-alcohol compound 2: (S)-[4-(methylsulfonyl)phenyl 1(R)-1-$R_1$-aziridin-2-yl]methanol;

compound 2

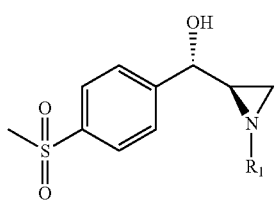

(4) heating the (S)-[4-(methylsulfonyl)phenyl][(R)-1-$R_1$-aziridin-2-yl]methanol and triethylamine trihydrofluoride in the solvent and facilitating the reaction to obtain (1S,2S)-3-fluorine-1-[4-(methylsulfonyl)phenyl]-2-($R_1$-amino)-1-propanol;

(5) performing the hydrogenation protection for the (1S,2S)-3-fluorine-1-[4-(methylsulfonyl)phenyl]-2-($R_1$-amino)-1-propanol in the solvent via Pd/C to obtain (1S,2S)-2-amino-3-1-[4-(methylsulfonyl)phenyl]-1-propanol;

(6) facilitating an acylation reaction and a cyclization reaction of the (1S,2S)-2-amino-3-1-[4-(methylsulfonyl)phenyl]-1-propanol to prepare a compound acylation 3, and facilitating the hydrolysis and acylation of the compound 3 to obtain florfenicol;

compound 3

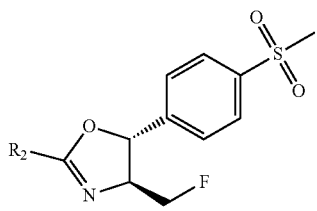

wherein R2 is phenyl or bischloromethyl or hydroxy.

Both of the technical solution of the present invention and the preceding invention (CN102827042A) of the applicant can produce the target product; in the view of the technological process, technological procedures before the preparation of the compound 2-bromo-3-chloro-1-[4-(methylsulfonyl)phenyl]-1-acetone can be shared, but the later reaction concept is completely different; Cn102827042A is to utilize the asymmetric reduction reaction of the chiral catalyst to build the chiral central carbon, while the present invention utilizes the cyclization of the chiral amine to build the chiral carbon and utilizes the despin characteristic of the compound to obtain the chiral compound by means of the physical resolution method.

The present invention aims at two big problems in the synthetic process of the florfenicol: I, only one compound needed from two chiral centers and four compounds; II, the introduction of fluorine atoms. The technological process of the present invention reasonably and effectively solves the two problems:

firstly, in the present invention, a pair of aziridine three-membered ring compounds of diastereoisomer chiral aminoketone are obtained by adopting the cyclization of chiral amine, the aziridine three-membered ring compound of the needed R-configuration aminoketone is obtained by utilizing the physical separation method, and the aziridine three-membered ring compound of the S-configuration aminoketone can be repeatedly purified by means of the despin characteristic in the solvent to obtain the needed R-configuration compound, so that the raw material basically has no loss, and the atom economy is greatly improved; additionally, the aziridine three-membered ring compound of the R-configuration aminoketone can be selectively reduced to obtain the single-configuration chiral aminoketone compound (referring to J. Org. Chem. 2003, 68, 7675-7680), and after the esterification reaction is performed by utilizing the hydroxyalkanesulfonic acid, the cyclization reaction is performed to realize the configuration transformation, thereby solving the chiral problem of florfenicol.

Secondly, by utilizing the characteristic that the aziridine three-membered ring is likely to have the nucleophilic reaction under the acid condition, triethylamine trihydrofluoride is used to have the ring-opening reaction with the aziridine three-membered ring to introduce the fluorine atoms. Triethylamine trihydrofluoride is liquid, the reaction temperature is not high, and the operation under pressure is not needed; moreover, the reagent has little corrosion on the equipment, so that the production safety is improved; therefore, the ring-opening reaction of the aziridine three-membered ring solves the introduction problem of the fluorine atoms.

In general, the first prominent advantage of the present invention is to obtain the single-R-configuration chiral aminoketone in high yield by utilizing the synthesizing method of the chiral amine closed-ring aziridine three-membered ring and by means of the repeated purification of the physical separation method; the florfenicol is finally obtained by utilizing the selective reduction and configuration transformation concept, so that the atom economy is greatly improved; and meanwhile, the waste water pollution in the prior art is avoided, the cost for treating the waste water and the environmental pollution are greatly reduced, the cost is reduced, and the technology is simplified. The second advantage is to adopt the triethylamine trihydrofluoride as the fluorination ring-opening reagent on the basis of the above-mentioned synthetic route; compared with the gas reaction, the safety of the liquid reaction is improved; and in addition, the corrosion to the equipment is small, thereby facilitating the industrialization production.

DETAILED DESCRIPTION OF PREFERRED EMBODIMENTS

The florfenicol synthesizing method of the present invention can be described representatively as the following technological process:

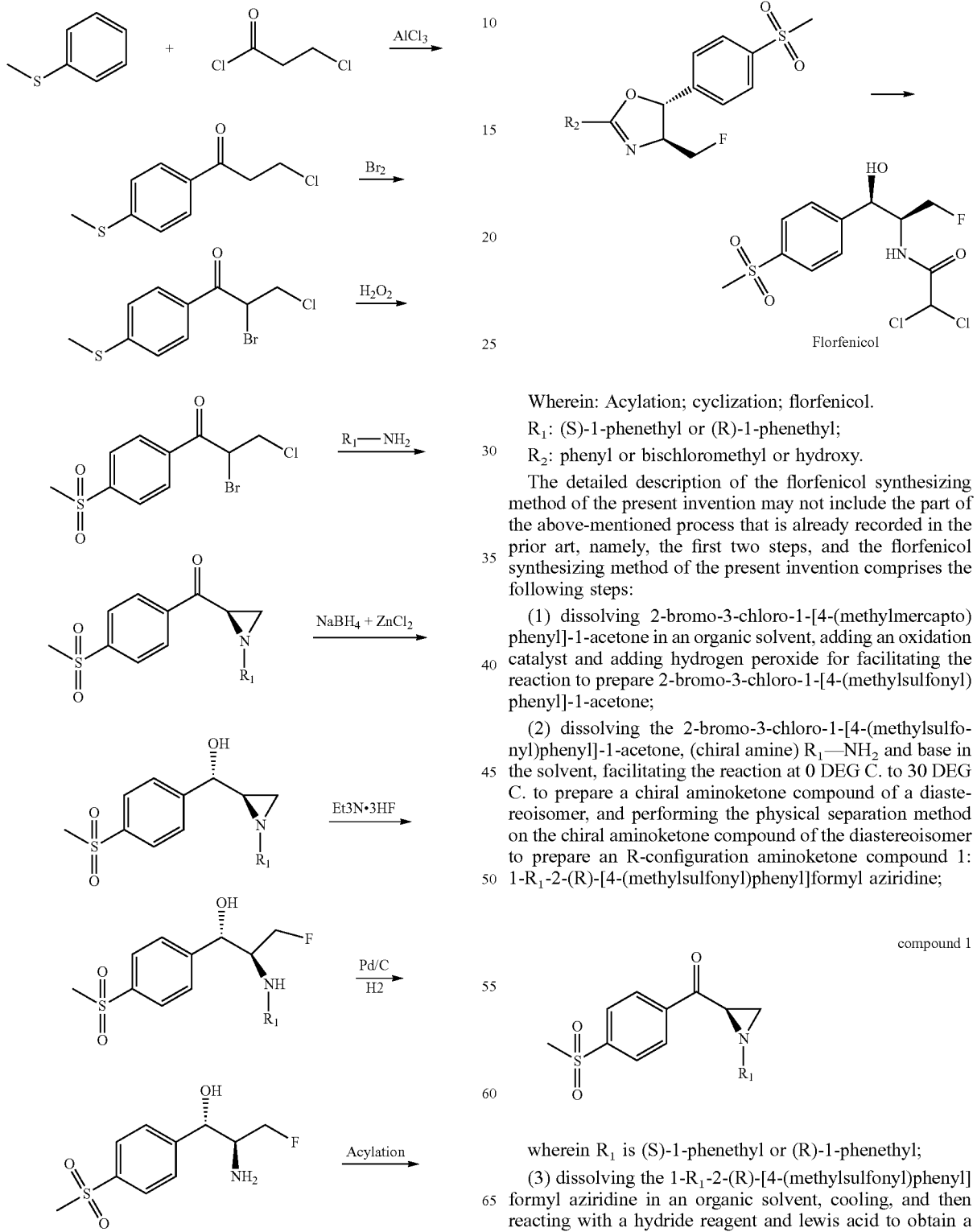

Wherein: Acylation; cyclization; florfenicol.

$R_1$: (S)-1-phenethyl or (R)-1-phenethyl;

$R_2$: phenyl or bischloromethyl or hydroxy.

The detailed description of the florfenicol synthesizing method of the present invention may not include the part of the above-mentioned process that is already recorded in the prior art, namely, the first two steps, and the florfenicol synthesizing method of the present invention comprises the following steps:

(1) dissolving 2-bromo-3-chloro-1-[4-(methylmercapto) phenyl]-1-acetone in an organic solvent, adding an oxidation catalyst and adding hydrogen peroxide for facilitating the reaction to prepare 2-bromo-3-chloro-1-[4-(methylsulfonyl) phenyl]-1-acetone;

(2) dissolving the 2-bromo-3-chloro-1-[4-(methylsulfonyl)phenyl]-1-acetone, (chiral amine) $R_1$—$NH_2$ and base in the solvent, facilitating the reaction at 0 DEG C. to 30 DEG C. to prepare a chiral aminoketone compound of a diastereoisomer, and performing the physical separation method on the chiral aminoketone compound of the diastereoisomer to prepare an R-configuration aminoketone compound 1: 1-$R_1$-2-(R)-[4-(methylsulfonyl)phenyl]formyl aziridine;

compound 1 wherein $R_1$ is (S)-1-phenethyl or (R)-1-phenethyl;

(3) dissolving the 1-$R_1$-2-(R)-[4-(methylsulfonyl)phenyl] formyl aziridine in an organic solvent, cooling, and then reacting with a hydride reagent and lewis acid to obtain a single-configuration chiral amino-alcohol compound 2:

(S)-[4-(methylsulfonyl)phenyl][(R)-1-$R_1$-aziridin-2-yl]methanol

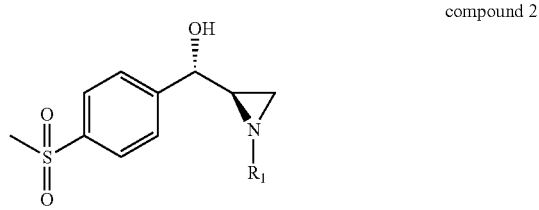

compound 2

(4) heating the (S)-[4-(methylsulfonyl)phenyl][(R)-1-$R_1$-aziridin-2-yl]methanol and triethylamine trihydrofluoride in the solvent for facilitating the reaction to obtain (1S,2S)-3-fluorine-1-[4-(methylsulfonyl)phenyl]-2-($R_1$-amino)-1-propanol;

(5) performing the hydrogenation and protection removal for the (1S,2S)-3-fluorine-1-[4-(methylsulfonyl)phenyl]-2-($R_1$-amino)-1-propanol in the solvent via Pd/C to obtain (1S,2S)-2-amino-3-1-[4-(methylsulfonyl)phenyl]-1-propanol;

(6) facilitating the acylation reaction and the cyclization reaction of the (1S,2S)-2-amino-3-1-[4-(methylsulfonyl)phenyl]-1-propanol, performing the esterification cyclization of hydroxyalkanesulfonic acid for facilitating the configuration transformation reaction to prepare a compound 3, and performing the hydrolysis and the acylation on the compound 3 to obtain florfenicol;

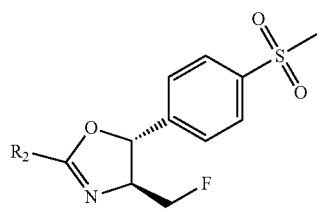

compound 3 wherein R2 is phenyl or bischloromethyl or hydroxy.

In one detailed description of the present invention, the acylation reaction of the step (6) is as follows: in the solvent, (1S,2S)-2-amino-3-fluoro-1-[4-(methylsulfonyl)phenyl]-1-propanol reacts with an acylation reagent and base for 2 hours-10 hours at 0 DEG C.-30 DEG C. according to the molar ratio of 1:1.0-3.0:1.2-4.0; the solvent is selected from one or more mixture of methanol, tetrahydrofuran, dichloromethane, trichloromethane and 1,2-dichloroethane; and the solvent is selected preferably from tetrahydrofuran, methanol or dichloromethane, and most preferably from tetrahydrofuran or dichloromethane.

The base is selected from potassium carbonate, sodium carbonate, sodium bicarbonate, potassium bicarbonate, triethylamine, diisopropylethylamine and pyridine, preferably from sodium carbonate and triethylamine, and most preferably from triethylamine.

The acylation reagent is selected from benzoyl chloride, methyl benzoate, ethyl benzoate, Boc anhydride, methyl dichloroacetate and ethyl dichloroacetate, preferably from benzoyl chloride and methyl dichloroacetate, and most preferably from methyl dichloroacetate.

In the detailed description of the present invention, the cyclization reaction of the step (6) is as follows: in the solvent, the raw material, the sulfonic acid esterification reagent and the base react for 2 hours-16 hours at 0 DEG C.-50 DEG C. according to a molar ratio of 1:1.0-3.0:1.2-5.0, wherein the raw material is a product obtained after the acetylation reaction of (1S,2S)-2-amino-3-fluoro-1-[4-(methylsufonyl)phenyl]-1-propanol in the step (6);

the solvent is selected from dichloromethane, trichloromethane, 1,2-dichloroethane and tetrahydrofuran, and preferably from dichloromethane;

the base is selected from potassium carbonate, sodium carbonate, sodium bicarbonate, potassium bicarbonate, triethylamine, diisopropylethylamine and pyridine, and preferably from triethylamine.

In the detailed description of the present invention, the reaction of the step (1) can be described in details as follows: in the solvent, in the existence of the oxidation catalyst, 2-bromo-3-chloro-1-[4-(methylmercapto)phenyl]-1-acetone, and hydrogen peroxide react for 6 hours-24 hours at 20 DEG C.-60 DEG C. according to a molar ratio of 1:2-10;

wherein the solvent is selected from methanol, ethanol, isopropanol and acetonitrile, and preferably from acetonitrile;

the catalyst is selected from potassium dichromate, chromium trioxide, manganese dioxide, ferric trichloride, tungstic acid sodium salt dihydrate, molybdenum trioxide, aluminum oxide, ferric oxide, acetic acid, dichloroacetic acid, trichloroacetic acid, trifluoroacetic acid and boric acid, and preferably from tungstic acid sodium salt dihydrate and trifluoroacetic acid.

The hydrogen peroxide is added in a dropwise manner, and when the hydrogen peroxide is dropwise added, the temperature in the reaction solution is controlled not to be higher than 60 DEG C.

In the detailed description of the present invention, in the step (2), 2-bromo-3-chloro-1-[4-(methylsulfonyl)phenyl]-1-acetone, $R_1$—$NH_2$ and base react for 2 hours-6 hours according to a molar ratio of 1:1.0-1.5:2.0-3.0;

the solvent is selected from dichloromethane, trichloromethane, 1,2-dichloroethane, methanol and ethanol, and the mass ratio of the solvent to the reactant is 5-20:1;

the base is selected from potassium carbonate, sodium carbonate, sodium bicarbonate, potassium bicarbonate, triethylamine, diisopropylethylamine and pyridine, and preferably from sodium carbonate, and most preferably from triethylamine.

In the detailed description of the present invention, the physical separation method in the step (2) is a column chromatography separation method or a recrystallization method;

wherein the column chromatography separation method adopts silica gel as a filling material, the meshes of the silica gel can be 100 meshes-400 meshes, the 300-mesh to 400-mesh silica gel is preferably selected, and a mixed solution of ethyl acetate and petroleum ether in a volume ratio of 1:10 to 1:1 is used as leacheate; and the solvent used in the recrystallization method is selected from one or more mixture of dichloromethane, trichloromethane, 1,2-dichloroethane, methylbenzene, xylene, methanol, ethanol, isopropanol, acetonitrile, acetone and ethyl acetate.

The physical separation method preferably selects the recrystallization method.

In the detailed description of the present invention, a step of collecting the recrystallized residual mother solution and re-separating the recrystallized residual mother solution after the self spin elimination to prepare a needed R-configuration product is further included.

In the detailed description of the present invention, the reaction molar ratio of the 1-$R_1$-2-(R)-[4-(methylsulfonyl)phenyl]formyl aziridine to the hydride reagent to the lewis acid is 1:0.5-2.0:0.5-1.5, and the reaction temperature is minus 50 DEG C.-10 DEG C.

The hydride reagent is selected from $NaBH_4$, $KBH_4$, $B_2H_6$, $LiAl(OCH_3)_3H$ and $LiAl(Ot-Bu)_3H$;

the lewis acid is selected from $CeCl_3$, $TiCl_4$, $CoCl_2$, $NiCl_2$ and $ZnCl_2$;

all organic solvents are selected from:

a, one or more mixture of methanol, ethanol and isopropanol, or b, one of dichloromethane, trichloromethane, tetrahydrofuran and dioxane solvent, or c, a mixture of any one of solvents in group b and any one of solvents in group a.

In the detailed description of the present invention, the reaction molar ratio of the compound 2 to the triethylamine trihydrofluoride in the step (4) is 1:1.2-10, and the reaction temperature is 50 DEG C.-110 DEG C.;

wherein the solvent is selected from dichloromethane, trichloromethane, 1,2-dichloroethane, tetrahydrofuran, dioxane, chlorobenzene, methylbenzene, xylene, ether, methyl tertiary butyl ether, isopropyl ether, dichloroether, NMP, DMF and DMSO, and the mass ratio of the solvent to the compound 2 is 3-15:1.

In the detailed description of the present invention, the mass ratio of (1S,2S)-3-fluoro-1-[4-(methylsulfonyl)phenyl]-2-($R_1$-amino)-1-propanol to Pd/C in the step (5) is 1:0.02-0.1, the reaction pressure is 1 atm-10 atm, and the temperature is 20 DEG C.-50 DEG C.;

Pd/C is a carbon-supported Pd catalyst, wherein the weight percentage content of Pd is 5%-10%; and the product facilitating the specification of 5% or 10% is preferred.

The solvent is selected from methanol, ethanol, isopropanol tetrahydrofuran and acetic acid.

In the above florfenicol synthesizing method of the present invention, the preparation of 2-bromo-3-chloro-1-[4-(methylsulfonyl)phenyl]-1-acetone can also be integrated, the preparation of the compound shall be used as previous procedures of the method of the present invention, and the preparation comprises the following steps:

(a) adding aluminum trichloride and 3-chloropropionyl chloride into dichloromethane, controlling the solution temperature at minus 5 DEG C.-10 DEG C., dropwise adding thioanisole, and performing the reaction at 0 DEG C.-50 DEG C. to obtain 3-chloro-1-[4-(methylmercapto)phenyl]-1-acetone;

(b) dissolving the 3-chloro-1-[4-(methylmercapto)phenyl]-1-acetone in dichloromethane or chloroform, keeping the solution temperature between minus 5 DEG C. and 10 DEG C., dropwise adding a dichloromethane or chloroform solution of bromine, after the solution is completely dropped, performing the reaction at minus 5 DEG C.-40 DEG C. to obtain 2-bromo-3-chloro-1-[4-(methylmercapto)phenyl]-1-acetone.

Wherein in the step (a), the molar ratio of 3-chloropropionyl chloride to aluminum trichloride to thioanisole is 1:1.0-1.6:1.0-1.5, and the reaction time is 1 hour-4 hours.

In the step (b), the molar ratio of 3-chloro-1-[4-(methylsufonyl)phenyl]-1-acetone to bromine is 1:1.0-1.3, and the reaction time is 0.5 hour-5 hours.

The non-limiting embodiments described below are used for further describing the florfenicol synthesizing method of the present invention. It shall be only appreciated that the embodiments below are only used for describing and supplementing the present invention, rather than limiting the technical solution of the present invention in any form.

Embodiment 1

Synthesizing 3-chloro-1-[4-(methylmercapto)phenyl]-1-acetone: adding aluminum trichloride (357 g, 2.68 mol) and 2000 ml of dichloromethane (pre-dried by means of anhydrous calcium chloride) into a 5 L reaction kettle at the room temperature; allowing the system to access a drying tube; stirring; pouring 3-chloropropionyl chloride (372 g, 2.93 mol) into a reaction bottle; cooling to 0 DEG C. by means of an ice bath; dropwise adding thioanisole (277 g, 2.23 mol) in 2 hours; after the dropwise addition is completed, transferring the reaction bottle into an oil bath; heating to 25 DEG C.; performing the reaction for 1 hour-3 hours; and monitoring by TLC until the reaction is ended. After half solvent is evaporated in a decompressing manner, the reaction solution is poured into the 10 L reaction kettle with 5 L of ice water, the reaction solution is stirred while being poured, after being completely added, the reaction solution is stirred for one hour, a great amount of solids are precipitated, the filtered solids are washed by utilizing a great amount of water and then dried, and the solids are recrystallized by utilizing dichloromethane to obtain 349 g of white acicular crystals, and the content detected by HPLC is 99.6%.

HNMR (400 Hz, DMSO-d6) δ 7.92 (d, J=8.8 Hz, 2H), 7.38 (d, J=8.4 Hz, 2H), 3.92 (m, 2H), 3.52 (m, 2H), 2.54 (s, 3H).

Embodiment 2

Synthesizing the compound 2-bromo-3-chloro-1-[4-(methylmercapto)phenyl]-1-acetone: adding 3-chloro-1-(4-(methylmercapto)phenyl)-1-acetone (160 g, 745 mmol) and 1800 ml of dichloromethane (pre-dried by anhydrous calcium chloride) into a 5000 ml three-opening bottle, and stirring; dropwise adding 40 ml of bromine (125 g, 780 mmol) and 200 ml of dichloromethane; uniformly stirring and mixing; then pouring into a constant-pressure dropping funnel; and placing the dropping funnel onto a reaction bottle. The reaction bottle is cooled in an ice-water bath, when the solution temperature is dropped to 0 DEG C., the dichloromethane solution of the bromine begins to be dropped, the temperature is kept at 0 DEG C., after the solution is completely dropped in 1 h-2 h, the temperature is kept at 0 DEG C. to facilitate the reaction, the TLC tracking is performed, after being completely dropped, the solution reacts for 1 hour, and the complete reaction is detected by means of TLC. A sodium bicarbonate saturated solution is added under the ice bath until the water phase is alkaline; then the solution is separated; an organic phase is added into a saturated sodium thiosulfate solution while in stirring until the organic phase becomes a colorless transparent solution; then the solution is separated; the organic phase is washed by utilizing a saturated saline solution, dried by anhydrous sodium sulfate, filtered and washed by dichloromethane; the filtrate and the washing solution are mixed to obtain a mixture, the rotary evaporation is performed on the mixture to remove the solvent to constant weight to obtain 215 g of white powdered solid, and the content detected by HPLC is 96.83%.

HNMR (400 Hz, $CDCl_3$) δ 7.96 (m, 2H), 7.38 (m, 2H), 5.27 (m, 1H), 4.36 (m, 1H), 3.96 (m, 1H), 2.56 (s, 3H).

Embodiment 3

Synthesizing the compound 2-bromo-3-chloro-1-[4-(methylsulfonyl)phenyl]-1-acetone: adding 160 g of 2-bromo-3-chloro-1-[4-(methylmercapto)phenyl]-1-acetone and 600 g of acetonitrile into a 2500 ml three-opening bottle; stirring to dissolve the raw material; adding 5 g of catalyst Na2WO4.2H2O; dropwise adding 375 g of 30% hydrogen peroxide; when the hydrogen peroxide is dropped, controlling the temperature in the reaction solution not to be higher than 60 DEG C.; after the hydrogen peroxide is completely added, performing the reaction for 16 hours at the room temperature; sampling, and monitoring by means of TLC or HPLC; after the reaction of the raw material is completed, quenching the reaction by adding 500 g of water; decompressing and spinning to remove a majority of acetonitrile solvent; precipitating a great amount of solids; after the solids are sucked and filtered, leaching the solids multiple times by utilizing 500 ml of water; and drying the solids to obtain 162 g of the compound, wherein the content detected by HPLC is 92%.

HNMR (400 Hz, CDCl$_3$) δ 8.22 (m, 2H), 8.14 (m, 2H), 5.28 (m, 1H), 4.36 (m, 1H), 3.98 (m, 1H), 3.12 (d, J=3.6 Hz, 3H).

When (S)-1-phenylethylamine is used as a raw material, the reaction route of cyclization is as follows:

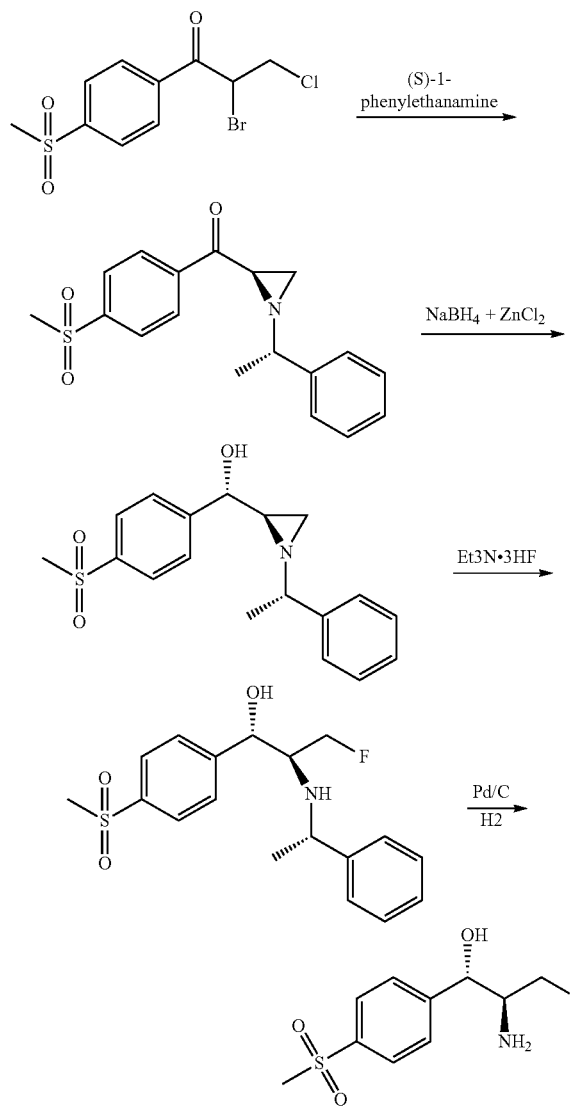

Embodiment 4

Synthesizing the compound 1-((S)-phenethyl)-2-(R)-[4-(methylsulfonyl)phenyl]formyl aziridine: adding 50 g (153 mmol) of 2-bromo-3-chloro-1-[4-(methylthio)phenyl]-1-acetone and 800 ml of methanol into a 1 L three-opening bottle; stirring to dissolve, adding 33 g (323 mmol) of triethylamine; cooling to about 10 DEG C.; dropwise adding a mixed solution of (S)-1-phenylethylamine (20 g, 165 mmol) and 50 ml of methanol; performing the reaction for 3 hours at the room temperature; detecting the completion of the reaction by means of TLC; spinning to remove the methanol: adding water to precipitate a great amount of white solids; washing the filtered solids with water; then washing the solids twice by utilizing 20 ml of absolute alcohol; drying the obtained solids to obtain 49.6 g of solids; recrystallizing the obtained solids by utilizing acetone; performing the self spin elimination on the recycled mother solution; and then repeatedly recrystallizing the recycled mother solution to finally obtain 40 g in total of 1-((S)-phenylethylamine)-2-(R)-[4-(methylsulfonyl)phenyl]formyl aziridine, wherein the content detected by HPLC is 99.2%, and the de value is 98.8%.

$[\alpha]^{20}_D$=+25.0 (c=2, CH2Cl2) LCMS: [M+Na] 330, [M+Na] 352

HNMR (400 MHz, CDCl$_3$) δ 7.89, 7.80), 7.80 (m, 2H), 7.26-7.41 (m, 5H), 3.04 (s, 3H), 2.84-2.87 (m, 1H), 2.71-2.76 (m, 1H), 2.62-2.63 (m, 1H), 2.02-2.04 (m, 1H), 1.54 (d, J=6.4 Hz, 3H).

Embodiment 5

Synthesizing the compound (S)-[4-(methylsulfonyl)phenyl][(R)-1-((S)-1-phenylethylamine)aziridine]methanol: in a 500 ml three-opening bottle, dissolving 20 g of 1-((S)-phenylethylamine)-2-(R)-[4-(methylsulfonyl)phenyl]formyl aziridine in 300 ml of methanol; adding 5 g of anhydrous ZnCl$_2$; stirring, and cooling to minus 40 DEG C.; after stirring half an hour, adding 3 g of NaBH4 in different steps; after the NaBH4 is completely added, performing the reaction for 4 hours at minus 40 DEG C.; monitoring the reaction solution by utilizing TLC; after the reaction of the raw material is completed, heating to the room temperature; quenching the reaction by adding water, spin-drying the methanol; adding dichloromethane; layering for extraction; spin-drying an organic layer to obtain a crude product; and recrystallizing the crude product by utilizing ethanol to obtain 18.2 g of products, wherein the content detected by HPLC is 96%, and the de value is 92%.

$[\alpha]^{20}_D$=−62.8 (c=4, CH2Cl2) LCMS: [M+1]332, [M+Na] 354

HNMR (400 MHz, CDCl$_3$) δ 7.80 (m, 2H), 7.43-7.45 (m, 2H), 7.22-7.33 (m, 5H), 4.67 (d, J=4.4 Hz, 1H), 3.35 (s, 1H), 3.03 (s, 3H), 2.64-2.68 (m, 1H), 2.04-2.08 (m, 1H), 1.84-1.88 (m, 1H), 1.44-1.48 (m, 3H).

Embodiment 6

Synthesizing the compound (1S,2S)-3-fluoro-1-[4-(methylsulfonyl)phenyl]-2-[((S)-1-phenethyl)amino]-1-propanol: in a 250 ml three-opening bottle, dissolving 18 g of compound (S)-[4-(methylsulfonyl)phenyl][(R)-1-((S)-1-phenylethylamine)aziridine]methanol in 180 g of 1,2-dichloroethane solution; adding 18 g of triethylamine trihydrofluoride, and heating to 85 DEG C.; refluxing to facilitate the reaction for 3 hours; monitoring the reaction by virtue of TLC or HPLC; after reaction of the raw material is completed, cooling to the room temperature; adding 80 ml of water to quench the reaction; adding 30 g of ammonia water; stirring to facilitate the reaction for 30 minutes; standing for layering; washing an organic layer twice by utilizing clean water; drying and spin-drying the organic layer to obtain 19.4 g of crude product; and directly utilizing the crude product in a next step without purification, wherein the purity detected by HPLC is 90%.

LCMS: [M+1] 1352, [M+Na] 374

HNMR (400 MHz, CDCl₃) δ 7.86-7.90 (m, 2H), 7.42-7.44 (m, 2H), 7.20-7.30 (m, 5H), 4.53-4.57 (m, 1H), 4.21-4.53 (m, 2H), 3.92-3.98 (m, 1H), 3.06 (s, 3H), 2.97-3.06 (m, 1H), 1.38-1.44 (m, 3H).

Embodiment 7

Synthesizing the compound (1S,2S)-2-amino-3-fluoro-1-[4-(methylsulfonyl)phenyl]-1-propanol: in a 250 ml three-opening bottle, adding 15 g of (1S,2S)-3-fluoro-1-[4-(methylsulfonyl)phenyl]-2-[((S)-1-phenethyl)amino]-1-propanol; dissolving in 120 g of methanol; adding 2 g of 10% Pd/C; performing the hydrogenation at 40 DEG C.; keeping the pressure of hydrogen at 1.2 atm; after the reaction is completed, filtering to remove the Pd/C; spin-drying the filtrate to obtain a crude product; pulping the crude product by utilizing isopropanol; and then filtering to obtain 9.6 g of product, wherein the purity detected by HPLC is 97%, and the ee value detected by Chiral-HPLC is 99.1%.

$[\alpha]^{20}_D$=+35.4 (c=2, CH₃OH) LCMS: [M+1] 248, [M+Na] 280

When (R)-1-phenylethylamine is used as a raw material, the reaction route of cyclization is as follows:

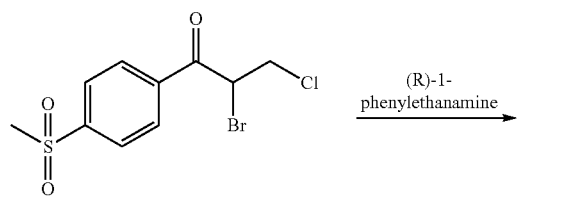

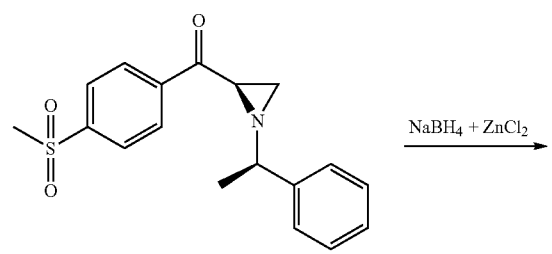

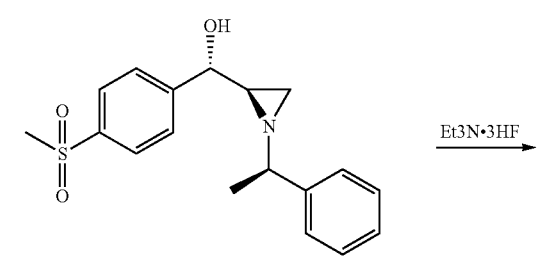

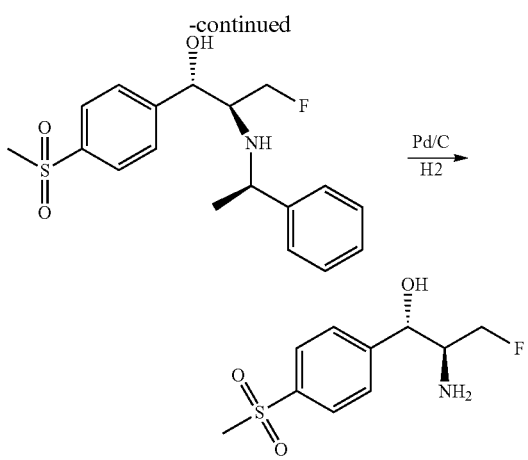

Embodiment 8

Synthesizing the compound 1-((R)-phenethyl)-2-(R)-[4-(methylsufonyl)phenyl]formyl aziridine: adding 50 g (153 mmol) of 2-bromo-3-chloro-1-[4-(methylthio)phenyl]-1-acetone and 800 ml of methanol in a 1 L three-opening bottle; stirring for dissolving adding 33 g (323 mmol) of triethylamine; cooling to about 10 DEG C.; dropwise adding a mixed solution of 1-(R)-phenylethylamine (20 g, 165 mmol) and 50 ml of methanol; performing the reaction for 3 hours at the room temperature; after the reaction is completed by virtue of the TLC detection, spinning to remove the methanol; adding water to precipitate a great amount of white solids; washing the filtered solids by utilizing water then washing the solids twice by utilizing 20 ml of absolute alcohol; drying the obtained solids to obtain 50.2 g of solids; allowing the obtained solids to first pass through a column (a silica gel column with 300 meshes to 400 meshes) by utilizing petroleum ether and ethyl acetate to perform the purification to obtain 20 g of pure product; performing the self-spin elimination on a cross product and the product of another configuration in the mixed solvent of dichloromethane and methanol; then purifying by utilizing the column to obtain 9.2 g of product; performing the self-spin elimination on the residual product; and repeatedly purifying the residual product to finally obtain 40.6 g in total of 1-((R)-phenethyl)-2-(R)-[4-(methylsulfonyl)phenyl]formyl aziridine, wherein the content detected by HPLC is 99.1%, and the de value is 98.6%.

LCMS: [M+1] 330, [M+Na] 352

HNMR (400 MHz, CDCl₃) δ 8.46-8.48 (m, 2H), 8.31-8.33 (m, 2H), 7.28-7.45 (m, 5H), 3.70-3.75 (m, 1H), 3.11 (s, 3H), 3.01-3.03 (m, 1H), 2.26-2.28 (m, 1H), 1.88-1.90 (m, 1H), 1.20-1.27 (m, 3H).

Embodiment 9

Synthesizing the compound (S)-[4-(methylsulfonyl)phenyl][(R)-1-((R)-1-phenylethylamine)aziridine]methanol: in a 500 ml three-opening bottle, dissolving 20 g of 1-((R)-phenylethylamine)-2-(R)-[4-(methylsulfonyl)phenyl]formyl aziridine in 300 ml of methanol; adding 5 g of anhydrous ZnCl₂; stirring, and cooling to minus 40 DEG C.; after stirring half an hour, adding 3 g of NaBH4 in different steps; after the NaBH4 is completely added, performing the reaction for 4 hours at minus 40 DEG C.; monitoring the reaction solution by utilizing TLC; after the reaction of the raw material is completed, heating to the room temperature; quenching the reaction by adding water; spin-drying the methanol; adding dichloromethane solution; layering for extraction; spin-drying an organic layer to obtain a crude product; and recrystallizing the crude product by utilizing ethanol to obtain 19.2 g of products, wherein the content detected by HPLC is 94%, and the de value is 90%. LCMS: [M+1] 352, [M+Na] 374

Embodiment 10

Synthesizing the compound (1S,2S)-3-fluoro-1-[4-(methylsulfonyl)phenyl]-2-[((R)-1-phenethyl)amino]-1-propanol: in a 250 ml three-opening bottle, dissolving 18 g of compound (S)-[4-(methylsulfonyl)phenyl][(R)-1-((R)-1-phenylethylamine)aziridine]methanol in 180 g of 1,2-dichloroethane solution; adding 18 g of triethylamine trihydrofluoride; heating to 85 DEG C.; refluxing for facilitating the reaction for 3 hours; monitoring the reaction by virtue of TLC or HPLC; after the reaction of the raw material is completed, cooling to the room temperature; adding 80 ml of water to quench the reaction; adding 30 g of ammonia water; stirring to facilitate the reaction for 30 minutes; standing for layering; washing an organic layer twice by utilizing clean water; drying and spin-drying the organic layer to obtain 18.2 g of crude product; and directly utilizing the crude product in a next step without purification, wherein the purity detected by HPLC is 89%. LCMS: [M+1] 332, [M+Na] 354

Embodiment 11

Synthesizing the compound (1S,2S)-2-amino-3-fluoro-1-[4-(methylsulfonyl)phen]-1-propanol: in a 250 ml three-opening bottle, adding 15 g of (1S,2S)-3-fluoro-1-[4-(methylsulfonyl)phenyl]-2-1((R)-1-phenethyl)aminol-1-propanol; dissolving in 120 g of methanol: adding 2 g of 10% Pd/C; performing the hydrogenation at 40 DEG C.; keeping the pressure of hydrogen at 1.2 atm; after the reaction is completed, filtering to remove the Pd/C; spin-drying the filtrate to obtain 9.4 g of crude products; pulping the crude products by utilizing isopropanol; and utilizing the crude products directly in the next step without purification, wherein the purity detected by HPLC is 95%, and the ee value detected by Chiral-HPLC is 98.3%.

$[\alpha]^{20}_D$=+34.6 (c=2, CH$_3$OH) LCMS: [M+1] 248, [M+Na] 280

When Boc is used as a protection group to perform the configuration transformation, a reaction route of the florfenicol amine is as follows:

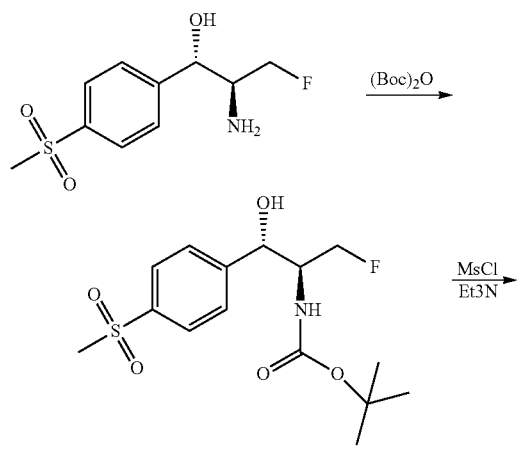

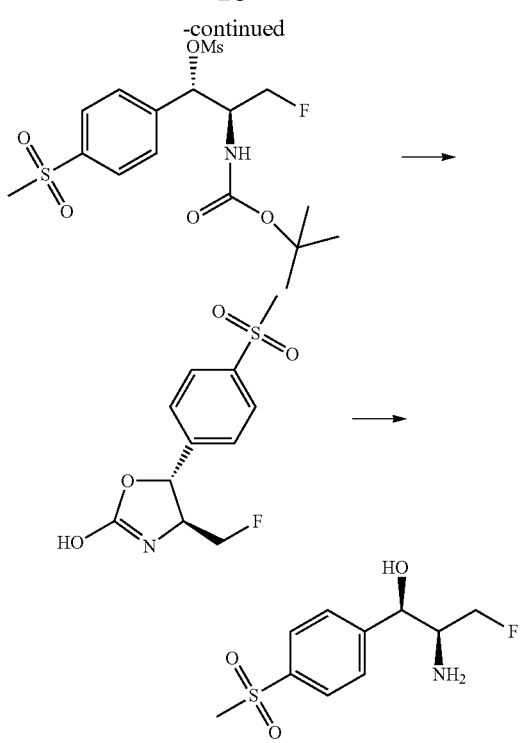

Embodiment 12

Synthesizing the compound (1S,2S)-3-fluoro-1-[4-(methylsulfonyl)phenyl]-2-[(Boc protection)amino]-1-propanol: in a 250 ml single-opening bottle, adding 15 g of (1S,2S)-2-amino-3-fluoro-1-[4-(methylsulfonyl)phenyl]-1-propanol; dissolving in 120 ml of THF; adding 13 g of sodium carbonate; adding 80 ml of water; after the dissolution, cooling to 0 DEG C.; weighing 16 g of Boc anhydride; dissolving in 30 ml of THF; dropwise adding the above Boc anhydride solution; after the anhydride solution is completely added, heating to the room temperature to facilitate the reaction for 4 hours; monitoring the completion of the reaction by virtue of TLC; standing for layering; extracting a water layer twice by utilizing dichloromethane; merging the organic layer drying, and spin-drying the solvent to obtain a crude product; pulping the crude product by utilizing the mixed solvent of ethyl acetate and petroleum ether; and filtering solids to obtain 19.1 g of products, wherein the purity detected by HPLC is 95%.

LCMS: [M+23] 370 [M−73] 274
HNMR (400 MHz, CDCl$_3$) δ 7.88-7.90 (m, 2H), 7.58-7.60 (m, 2H), 4.97-5.01 (m, 2H), 4.37-4.78 (m, 2H), 3.92-4.12 (m, 1H), 3.02 (s, 3H), 1.34 (m, 9H)

Embodiment 13

Synthesizing the compound (1S,2S)-3-fluoro-1-[4-(methylsulfonyl)phenyl]-2-[(Boc protection)amino]-1-propanol methyl sulfonate: in a 250 ml three-opening bottle, adding 16 g of (1S,2S)-3-fluoro-1-[4-(methylsulfonyl)phenyl]-2-[(Boc protection)amino]-1-propanol; dissolving in 120 ml of THF; adding 9.3 g of triethylamine; cooling to 0 DEG C.; dropwise adding 6.6 g of methylsufonyl chloride; after the methylsufonyl chloride is completely added, performing the reaction at room temperature; staying overnight; after the completion of the reaction is monitored by virtue of TLC, adding 50 ml of water to quench the reaction; standing for layering; extracting a water layer by utilizing dichloromethane; spin-drying an organic layer to obtain 18.2 g of crude product, and utilizing the crude product directly in the next step without purification, wherein the purity detected by HPLC is 90%.

LCMS: [M+23]: 448 [M−152]: 274

HNMR (400 MHz, CDCl₃) δ 7.98-8.03 (m, 2H), 7.65-7.67 (m, 2H), 5.71-5.73 (m, 1H), 4.96-4.98 (m, 1H), 4.43-4.83 (m, 2H), 4.16-4.30 (m, 1H), 3.05 (s, 3H), 2.93 (s, 3H), 1.26-1.28 (m, 9H).

Embodiment 14

Synthesizing the compound (4S,5R)-4-methyl fluoride-5-4-methylsulfone phenyl-2-hydroxyl-4,5-dihydrooxazole: in a 250 ml single-opening bottle, dissolving 16 g of (1S,2S)-3-fluoro-1-[4-(methylsulfonyl)phenyl]-2-[(Boc protection) amino]-1-propanol methyl sulfonate in 150 ml of tetrahydrofuran; adding 3.7 g of triethylamine; heating to 60 DEG C. to facilitate the reaction for 2 hours; after the completion of the reaction is monitored by virtue of TLC, spin-drying the tetrahydrofuran; adding 100 ml and 30 ml of water, stirring for 10 minutes; standing for layering; washing an organic layer by utilizing a sodium carbonate solution; washing with water, and spin-drying to obtain 9.1 g of product, wherein the purity detected by HPLC is 95%.

LCMS: [M+1] 274 [M+Na] 374

HNMR (400 MHz, CDCl₃) δ 8.01-8.03 (m, 2H), 7.59-7.61 (m, 2H), 5.85 (s, 1H), 5.47-5.48 (m, 1H), 5.30 (s, 1H), 4.50-4.68 (m, 2H), 3.93-4.01 (m, 1H), 3.07 (s, 3H)

Embodiment 15

Synthesizing the compound (florfenicol amine) (1R,2S)-2-amino-3-fluoro-1-[4-(methylsulfonyl)phenyl]-1-propanol: in a 250 ml single-opening bottle, dissolving 7 g of (4S, 5R)-4-methyl fluoride-5-4-methylsulfone phenyl-2-hydroxyl-4,5-dihydrooxazole in 130 ml of methanol; adding 64 ml of 4NKOH aqueous solution; heating to 70 DEG C.; refluxing for 24 hours; after the completion of the reaction is monitored by virtue of TLC and the solvent is decompressed and evaporated, extracting by utilizing the dichloromethane; drying an organic layer; spin-drying to obtain a crude product; and recrystallizing the crude product by utilizing isopropanol to obtain 4.6 g of products, wherein the purity detected by HPLC is 95%, and the ee value detected by Chiral-HPLC is 99.4%.

[α]²⁰_D=−35.2 (c=2, CH₃OH) LCMS: [M+1] 248, [M+Na] 280

When benzoyl is used as a protection group to perform the configuration transformation, a reaction route of the florfenicol amine is as follows:

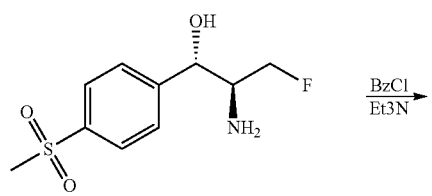

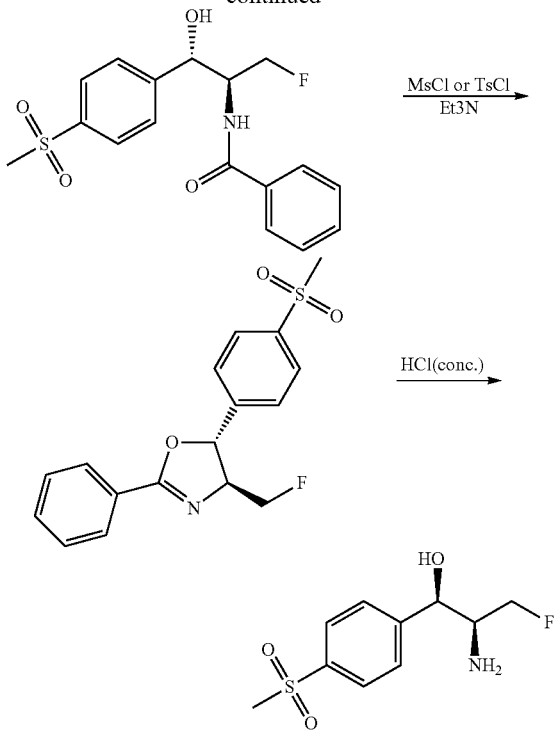

Embodiment 16

Synthesizing the compound (1S,2S)-3-fluoro-1-[4-(methylsulfonyl)phenyl]-2-[(benzoyl)amino]-1-propanol: in a 250 ml single-opening bottle, adding 12.4 g of (1R,2S)-2-amino-3-fluoro-1-[4-(methylsulfonyl)phenyl]-1-propanol, dissolving in 150 g of dichloromethane; adding 7.6 g of triethylamine; cooling to a temperature below zero; weighing 7.1 g of benzoyl chloride; diluting with 20 g of dichloromethane; dropwise adding into a reaction solution to obtain a mixed solution; during the dropwise addition, controlling the temperature of the reaction solution to be lower than 0 DEG C.; after the mixed solution is completely added, performing the reaction for 2 hours at 0 DEG C.-10 DEG C.; monitoring by virtue of TLC; after the reaction is completed, adding 80 ml of water to quench the reaction; precipitating the white solids; decompressing and evaporating the dichloromethane solvent; filtering the solids; washing a filter cake twice; drying the solids to obtain 17.2 g of crude products, and recrystallizing the crude products with isopropanol to obtain 16.2 g of products, wherein the HPLC purity is 95%.

LCMS: [M+1] 352[M+Na] 374

HNMR (400 MHz, DMSO-d6) δ 8.55-8.57 (m, 1H), 7.86-7.88 (m, 2H), 7.68-7.73 (m, 4H), 7.42-7.53 (m, 3H), 6.04 (m, 1H), 4.55-4.90 (m, 3H), 4.35-4.42 (m, 1H), 3.16 (s, 3H).

Embodiment 17

Synthesizing the compound (4S,5R)-4-methyl fluoride-5-4-methylsulfone phenyl-4,5-dihydrooxazole: in a 250 ml three-opening bottle, dissolving 15 g of (1 S,2S)-3-fluoro-1-[4-(methylsulfonyl)phenyl]-2-[(benzoyl)amino]-1-propanol into 150 ml of dichloromethane; adding 6.5 g of triethylamine; cooling to 0 DEG C.; weighing 5.9 g of methylsufonyl chloride; dropwise adding the methylsufonyl chloride into a solution; controlling the reaction temperature to be lower than 15 DEG C.; after the methylsufonyl chloride is completely added, cooling the reaction solution to room temperature to facilitate the reaction; staying overnight; after the reaction is completed, adding 50 ml of water to quench the reaction; stirring for 30 minutes; standing for layering; washing an organic layer twice with clean water; spin-drying the organic layer to obtain a crude product; and recrystallizing the crude product with ethanol to obtain 12.1 g of products, wherein the content detected by HPLC is 95%.

LCMS: [M+1] 334[M+Na] 356

HNMR (400 MHz, CDCl$_3$) δ 7.96-8.05 (m, 4H), 7.45-7.57 (m, 5H), 5.66-5.68 (m, 1H), 4.56-4.85 (m, 2H), 4.34-4.43 (m, 1H), 3.05 (s, 3H).

Embodiment 18

Synthesizing the compound (4S,5R)-4-methyl fluoride-5-4-methylsulfone phenyl-4,5-dihydrooxazole: in a 250 ml three-opening bottle, dissolving 15 g of (1 S,2S)-3-fluoro-1-[4-(methylsulfonyl)phenyl]-2-[(benzoyl)amino]-1-propanol in 150 ml of dichloromethane; adding 6.5 g of triethylamine; cooling to 0 DEG C.; weighing 17.3 g of p-methyl benzene sulfonic chloride; dropwise adding the methylsufonyl chloride into a solution; controlling the reaction temperature to be lower than 15 DEG C.; after the methylsufonyl chloride is completely added, cooling the reaction solution to room temperature to facilitate the reaction; staying overnight; after the reaction is completed, adding 50 ml of water to quench the reaction; stirring for 30 minutes; standing for layering; washing an organic layer twice with clean water; spin-drying the organic layer to obtain a crude product, and recrystallizing the crude product with ethanol to obtain 10.2 g of products, wherein the content detected by HPLC is 96%.

Embodiment 19

Synthesizing the compound (florfenicol amine) (1R,2S)-2-amino-3-fluoro-1-[4-(methylsulfonyl)phenyl]-1-propanol: in a 250 ml single-opening bottle, dissolving g of (4S,5R)-4-methyl fluoride-5-4-methylsulfone phenyl-2-phenyl-4,5-dihydrooxazole in 30 ml of ethanol; adding 50 ml of concentrated hydrochloric acid; heating to 100 DEG C., and performing the reaction and refluxing for 8 hours; monitoring by virtue of TLC; after the reaction of the raw material is completed, decompressing and evaporating the ethanol; extracting the residual water layer twice with dichloromethane; spin-drying the water phase; adding ammonia water; precipitating a great amount of white solids, and drying the solids to obtain 6.6 g of products, wherein the purity detected by HPLC is 97%, and the ee value detected by Chiral-HPLC is 99.5%.

$[\alpha]^{20}_D = -35.5$ (c=2, CH$_3$OH) LCMS: [M+1] 248, [M+Na] 280

When dichloroacetyl is used as a protection group to perform the configuration transformation, a reaction route of the florfenicol is as follows:

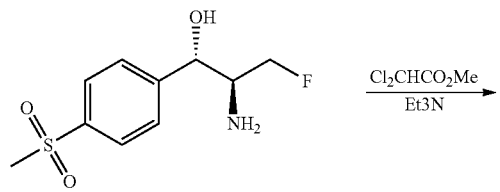

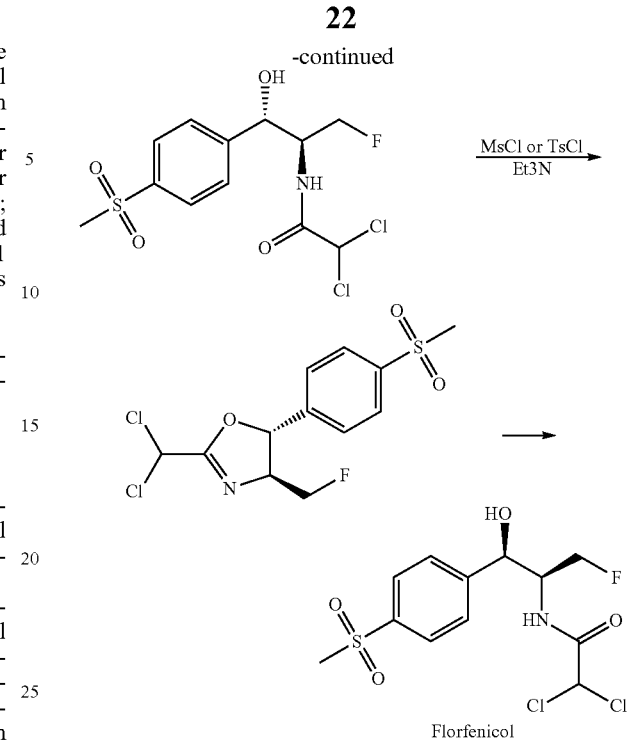

Florfenicol

Embodiment 20

Synthesizing the compound (1S,2S)-3-fluoro-1-[4-(methylsulfonyl)phenyl]-2-[(dichloroacetyl)amino]-1-propanol:
in a 250 ml single-opening bottle, adding 9.6 g of (1R,2S)-2-amino-3-fluoro-1-[4-(methylsulfonyl)phenyl]-1-propanol, and dissolving in 50 g of methanol; adding 11.8 g of triethylamine; adding 13.8 g of methyl dichloroacetate; heating to 50 DEG C., and performing the reaction for 8 hours; monitoring by virtue of TLC; after the reaction is completed, decompressing and spin-drying the methanol; adding 20 ml of 1N HCl; stirring for 20 minutes, and precipitating solids; filtering and drying the solids to obtain 13.1 g of crude products; recrystallizing the crude products with isopropanol to obtain 12.2 g of products, wherein the HPLC purity is 95%.

LCMS: [M+1] 358 360 [M+Na] 380 382

Embodiment 21

Synthesizing the compound (4S,5R)-2-bischloromethyl-4-methyl fluoride-5-4-methylsulfone phenyl-4,5-dihydrooxazole: in a 250 ml three-opening bottle, dissolving 12.5 g of (1S,2S)-3-fluoro-1-[4-(methylsulfonyl)phenyl]-2-[(dichloroacetyl)amino]-1-propanol in 100 g of dichloromethane; adding 5.3 g of triethylamine, stirring, and cooling to 0 DEG C.; weighing 4.8 g of methylsufonyl chloride; dropwise adding the methylsufonyl chloride into a solution; controlling the reaction temperature to be lower than 15 DEG C.; after the methylsufonyl chloride is completely added, cooling the reaction solution to room temperature to facilitate the reaction; staying overnight; after the reaction is completed, adding 50 ml of water to quench the reaction; stirring for 10 minutes; standing for layering; washing an organic layer twice with clean water; spin-drying the organic layer to obtain a crude product; recrystallizing the crude product with isopropanol to obtain 9.6 g of products, wherein the content detected by HPLC is 97%.

LCMS: [M+1] 340 342 [M+Na] 362 364

Embodiment 22

Synthesizing the compound (4S,5R)-2-bischloromethyl-4-methyl fluoride-5-4-methylsulfone phenyl-4,5-dihydrooxazole: in a 250 ml three-opening bottle, dissolving 8.2 g of (1S,2S)-3-fluoro-1-[4-(methylsulfonyl)phenyl]-2-[(dichloroacetyl)amino]-1-propanol in 100 g of dichloromethane; adding 4.6 g of triethylamine, stirring, and cooling to 0 DEG C.; weighing 6.5 g of p-methyl benzene sulfonic chloride; dropwise adding the p-methyl benzene sulfonic chloride into a solution; controlling the reaction temperature to be lower than 15 DEG C.; after the p-methyl benzene sulfonic chloride is completely added, cooling the reaction solution to room temperature to facilitate the reaction, and staying overnight; after the reaction is completed, adding 40 ml of water to quench the reaction; stirring for 10 minutes; standing for layering; washing an organic layer twice with clean water; spin-drying the organic layer to obtain a crude product; recrystallizing the crude product with isopropanol to obtain 5.8 g of product, wherein the content detected by HPLC is 97%.

Embodiment 23

Synthesizing the compound florfenicol: weighing 9.6 g of (4S,5R)-2-methyl fluoride-5-4-methylsulfone phenyl-dihydrooxazole, and adding into a 100 ml single-opening bottle; adding 50 ml of isopropanol and 20 ml of water; heating to 80 DEG C.; refluxing for 1 hour; monitoring the reaction by TLC; after the reaction is completed, adding 1 g of activated carbon to perform the decoloring for 30 minutes; filtering the activated carbon when the activated carbon is hot; leaching the activated carbon twice with hot isopropanol; decompressing and concentrating a mother solution until the isopropanol is dried; cooling by adding water to 5 DEG C.; sucking and filtering to obtain a crude product; recrystallizing the crude product with isopropanol and water to obtain 9.2 g of product, wherein the purity detected by HPLC is 98.6%.

Mp 152.3-154.6 DEG C.; $[\alpha]^{20}_D = -17.5$ (c=5, DMF)

The reaction route for synthesizing the florfenicol from florfenicol amine:

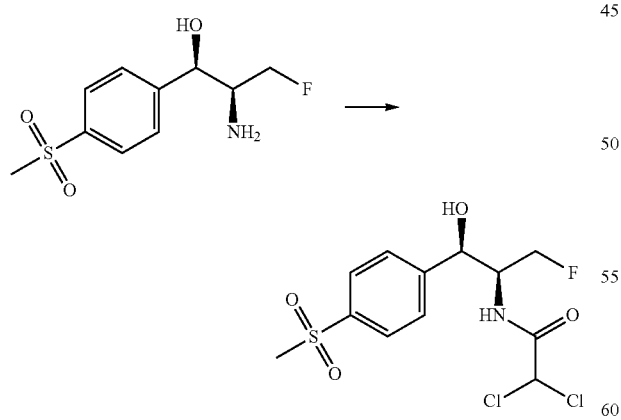

Embodiment 24

Synthesizing the compound florfenicol: in a 100 ml single-opening bottle; adding 5 g of florfenicol amine; dissolving into 25 ml of methanol; adding 6.1 g of triethylamine; adding 7.2 g of methyl dichloroacetate; heating to 50 DEG C. to facilitate the reaction for 12 hours; monitoring by virtue of TLC; after the reaction is completed, spin-removing the methanol; adding 30 ml of 1NHCl, and stirring to facilitate the reaction for 30 minutes; precipitating a great amount of white solids; filtering the solids to obtain a crude product; recrystallizing the crude product with a mixed solvent of isopropanol and water to obtain 6.5 g of product, wherein the HPLC purity is 98.4%.

Mp 152.5-154.4 DEG C.; $[\alpha]^{20}_D = -17.8$ (c=5, DMF)

We claim:
1. A method for synthesizing florfenicol, comprising the following steps:
   (1) dissolving 2-bromo-3-chloro-1-[4-(methylmercapto)phenyl]-1-acetone (compound 4) in an organic solvent and then adding an oxidation catalyst and hydrogen peroxide to produce 2-bromo-3-chloro-1-[4-(methylsulfonyl)phenyl]-1-acetone (compound 5)

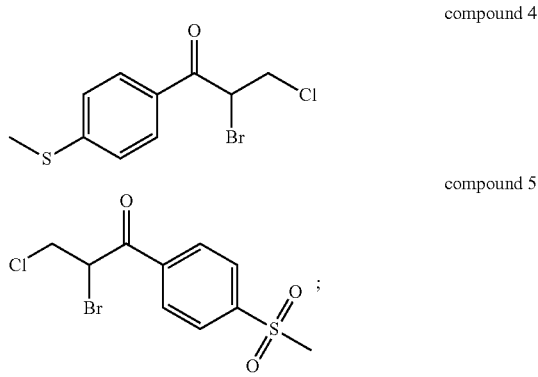

(2) dissolving the 2-bromo-3-chloro-1-[4-(methy sulfonyl)phenyl]-1-acetone (compound 5), a chiral amine of formula $R_1$—$NH_2$ and a base in an organic solvent to produce a reaction mixture, reacting the reaction mixture at 0 to 30° C. to prepare a mixture of chiral aminoketone diastereoisomers, and then performing a physical separation method on the mixture of chiral aminoketone diastereoisomers to obtain an R-configuration aminoketone of compound 1: 1-$R_1$-2-(R)-[4-(methylsulfonyl)phenyl]formyl aziridine

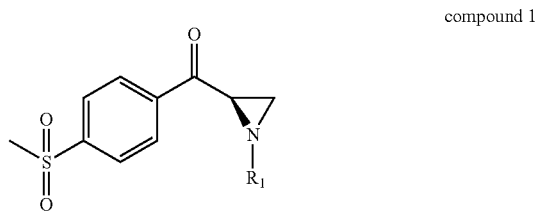

wherein $R_1$ is (S)-1-phenethyl or (R)-1-phenethyl;
(3) dissolving the 1-$R_1$-2-(R)-[4-(methylsulfonyl)phenyl] formyl aziridine in an organic solvent to form a mixture, and then adding a hydride reagent and a Lewis acid to the mixture and reacting at −50 to 10° C. to produce a chiral amino-alcohol compound 2: (S)-[4-(methylsulfonyl)phenyl][(R)-1-$R_1$-aziridin-2-yl] methanol as a single enantiomer

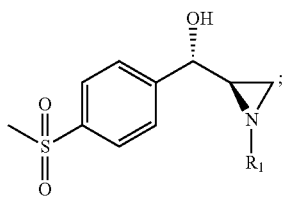
compound 2

(4) heating the (S)-[4-(methylsulfonyl)phenyl][(R)-1-$R_1$-aziridin-2-yl] methanol and triethylamine trihydrofluoride in an organic solvent and reacting at 50 to 110° C. to produce (1S,2S)-3-fluorine-1-[4-(methylsulfonyl)phenyl]-2-($R_1$-amino)-1-propanol (compound 6)

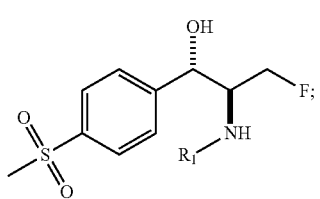
compound 6

(5) hydrogenating the (1S,2S)-3-fluorine-1-[4-(methylsulfonyl)phenyl]-2-($R_1$-amino)-1-propanol (compound 6) in an organic solvent in the presence of Pd/C catalyst at 1 to 10 atmos and 20 to 50° C. to produce (1S,2S)-2-amino-3-1-[4-(methylsulfonyl)phenyl]-1-propanol (compound 7)

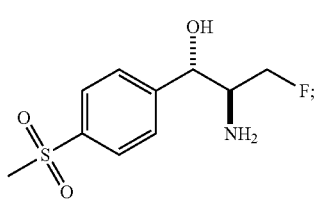
compound 7

(6) acylating the (1S,2S)-2-amino-3-1-[4-(methylsulfonyl)]-1-propanol (compound 7) with an acylation reagent having a group $R_2$ and cyclizing the acylated compound in the presence of a sulfonyl chloride esterification reagent in order to produce compound 8,

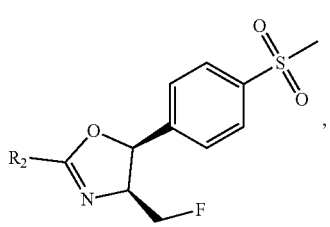
compound 8 wherein $R_2$ is phenyl, bischloromethyl or hydroxyl,
epimerizing the carbon atom of compound 8 that is attached to the oxygen atom and the phenyl ring to produce compound 3,

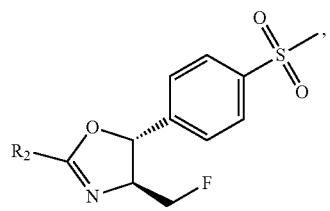
compound 3 and producing florfenicol through the hydrolysis of compound 3 when $R_2$ is bischloromethyl or
producing florfenicol through hydrolysis and subsequent acylation with a bischloromethyl acylating agent when $R_2$ is phenyl or hydroxyl

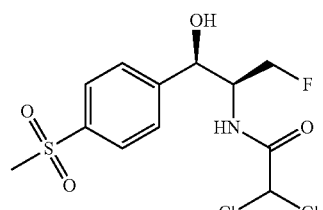
florfenicol

2. The method for synthesizing florfenicol according to claim 1, wherein in first acylation step of the step (6), (1S,2S)-2-amino-3-fluoro-1-[4-(methylsulfonyl)phenyl]-1-propanol is reacted with the acylation reagent having a group $R_2$ and a base in an organic solvent for 2 to 10 hours at 0 to 30° C., and wherein a molar ratio of (1S,2S)-2-amino-3-fluoro-1-[4-(methylsulfonyl)phenyl]-1-propanol (compound 7): the acylation reagent having a group $R_2$: the base is 1:1.0-3.0:1.2-4.0;

wherein the organic solvent used in the first acetylation step of the step (6) is selected from the group consisting of methanol, tetrahydrofuran dichloromethane, trichloromethane, 1,2-dichloroethane and mixtures thereof, wherein the base is selected from the group consisting of potassium carbonate, sodium carbonate, sodium bicarbonate, potassium bicarbonate, triethylamine, diisopropylethylamine and pyridine, and wherein the acylation reagent having a group $R_2$ is selected from the group consisting of benzoyl chloride, methyl benzoate, ethyl benzoate, methyl dichloroacetate and ethyl dichloroacetate.

3. The method for synthesizing florfenicol according to claim 1, wherein the cyclization step in the step (6) comprises reacting the acylated compound from the first acylation step in an organic solvent in the presence of the sulfonyl chloride esterification reagent and a base for 2 to 16 hours at 0 to 30° C., wherein a molar ratio of the acylated compound from the first acylation step: the sulfonyl chloride esterification reagent: base is 1:0-3.0:1.2-5.0;

wherein the organic solvent used in the cyclization step of the step (6) is selected from the group consisting of dichloromethane, trichloromethane, 1,2-dichloroethane and tetrahydrofuran; and wherein the base is selected from the group consisting of potassium carbonate, sodium carbonate, sodium bicarbonate, potassium bicarbonate, triethylamine, diisopropylethylamine and pyridine.

4. The method for synthesizing florfenicol according to claim 1, wherein in the step (1), 2-bromo-3-chloro-1-[4-(methylmercapto)phenyl]-1-acetone is reacted in the organic solvent with the oxidation catalyst and the hydrogen peroxide for 6 to 24 hours at 20 to 60° C., wherein a molar ratio of 2-bromo-3-chloro-1-[4-(methylmercapto)phenyl]-1-acetone to hydrogen peroxide is 1:2-10, wherein the organic solvent used in the step (1) is selected from the group consisting of methanol, ethanol, isopropanal and acetonitrile; and wherein the catalyst is selected from the group consisting of potassium dichromate, chromium trioxide, manganese dioxide, ferric trichloride, tungstic acid sodium salt dihydrate, molybdenum trioxide, aluminum oxide, ferric oxide, acetic add, dichloroacetic acid, trichloroacetic acid, trifloroacetic acid and boric acid.

5. The method for synthesizing florfenicol according to claim 1, wherein in the step (2), 2-bromo-3-chloro-1-[4-(methylsulfonyl)phenyl]-1-acetone is reacted with the chiral amine of formula $R_1$—$NH_2$ and the base in the organic solvent for 2 to 6 hours, wherein a molar ratio of 2-bromo-3-chloro-1-[4-(methylsulfonyl)phenyl]-1-acetone: the chiral amine of formula $R_1$—$NH_2$: the base is 1:1.0-1.5:2.0-3.0;

wherein the organic solvent used in the step (2) is selected from the group consisting of dichloromethane, trichloromethane, 1,2-dichloroethane, methanol and ethanol, and a weight ratio of the organic solvent to the reactants is 5-20:1; and wherein the base is selected from the group consisting of potassium carbonate, sodium carbonate, sodium bicarbonate, potassium bicarbonate, triethylamine, diisopropylethylamine and pyridine.

6. The method for synthesizing florfenicol according to claim 1, wherein the physical separation method in the step (2) is a column chromatography separation method or a recrystallization method; and when the physical separation method is the column chromatography separation method, silica gel of 100 to 400 mesh is used as a filling material, and a mixture of ethyl acetate and petroleum ether in a volume ratio of 1:10 to 1:1 is used as eluent; and when the physical separation method is the crystallization separation method, a solvent selected from the group consisting of dichloromethane, trichloromethane, 1,2-dichloroethane, methylbenzene, xylene, methanol, ethanol, isopropanol, acetonitrile, acetone, ethyl acetate and mixtures thereof is used.

7. The method for synthesizing florfenicol according to claim 6, wherein the recrystallization separation method further comprises the following steps:

collecting residual solution after recrystallization and
re-separating the residual solution, after autoracemization, to produce more of compound 1.

8. The method for synthesizing florfenicol according to claim 1, wherein in the step (3), a molar ratio of 1-$R_1$-2-(R)-[4-(methylsulfonyl)phenyl]formyl aziridine:hydride reagent: Lewis acid is 1:0.5-2.0:0.5-1.5; and wherein the hydride reagent is selected from the group consisting of $NaBH_4$, $KBH_4$, $B_2H_6$, $LiAl(OCH_3)_3H$ and $LiAl(Ot-Bu)_3H$;

wherein the Lewis acid is selected from the group consisting of $CeCl_3$, $TiCl_4$, $CoCl_2$, $NiCl_2$ and $ZnCl_2$; and wherein the organic solvent used in the step (3) is one of the following:
a. methanol, ethanol, isopropanol or a mixture thereof;
b. dichloromethane, trichloromethane, tetrahydrofuran or dioxane; or
c. a mixture of any one of the solvents from group b and any one of the solvents from group a.

9. The method for synthesizing florfenicol according to claim 1, wherein in the step (4), a molar ratio of compound 2 to triethylamine trihydrofluoride is 1:1.2-10; and wherein the organic solvent used in the step (4) is selected from the group consisting of dichloromethane, trichloromethane, 1,2-dichloroethane, tetrahydrofuran, dioxane, chlorobenzene, methylbenzene, xylene, ether, methyl tertiary butyl ether, isopropyl ether, dichloroether, NMP, DMF and DMSO, and wherein a weight ratio of the organic solvent to compound 2 is 3-15:1.

10. The method for synthesizing florfenicol according to claim 1, wherein in the step (5), a weight ratio of (1S,2S)-3-fluoro-1-[4-(methylsulfonyl)phenyl]-2-($R_1$-amino)-1-propanol to Pd/C catalyst is 1:0.02-0.1; and wherein the Pd/C catalyst is a carbon-supported Pd in which Pd is 5 to 10% by weight; and wherein the organic solvent used in the step (5) is selected from the group consisting of methanol, ethanol, isopropanol, tetrahydrofuran and acetic acid.

11. The method for synthesizing florfenicol according to claim 1, wherein the method further includes preparation of 2-bromo-3-chloro-1-[4-(methylmercapto)phenyl]-1-acetone comprising the following steps:

(a) adding aluminum trichloride and 3-chloropropionyl chloride to dichloromethane, dropwise adding thioanisole at −5 to 10° C. and then reacting at 0 to 50° C. for 1 to 4 hours to produce 3-chloro-1-[4-(methylmercapto)phenyl]-1-acetone; and (b) dissolving the 3-chloro-1-[4-(methylmercapto)phenyl]-1-acetone in dichloromethane or chloroform, dropwise adding solution of bromine in dichloromethane or chloroform at −5 to 10° C. and then reacting at −5 to 40° C. for 0.5 to 5 hours to produce 2-bromo-3chloro-1-[4-(methylmercapto)phenyl]-1-acetone.

12. The method for synthesizing florfenicol according to claim 11, wherein in the step (a), a molar ratio of 3-chloropropionyl chloride:aluminum trichloride:thioanisole is 1:1.0-1.6:1.0-1.5.

13. The method for synthesizing florfenicol according to claim 11, wherein in the step (b), a molar ratio of 3-chloro-1-[4-(methylmercapto)phenyl]-1-acetone to bromine is 1:0.1-1.3.

* * * * *